United States Patent
Howard et al.

(10) Patent No.: US 9,956,394 B2
(45) Date of Patent: May 1, 2018

(54) CONNECTORS FOR ELECTRICAL STIMULATION SYSTEMS AND METHODS OF MAKING AND USING

(71) Applicant: Boston Scientific Neuromodulation Corporation, Valencia, CA (US)

(72) Inventors: Joshua Dale Howard, Sacramento, CA (US); Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

(21) Appl. No.: 15/261,610

(22) Filed: Sep. 9, 2016

(65) Prior Publication Data
US 2017/0072187 A1    Mar. 16, 2017

Related U.S. Application Data

(60) Provisional application No. 62/216,594, filed on Sep. 10, 2015.

(51) Int. Cl.
| | |
|---|---|
| *A61N 1/00* | (2006.01) |
| *A61N 1/05* | (2006.01) |
| *A61N 1/375* | (2006.01) |
| *H01R 13/621* | (2006.01) |
| *H01R 24/58* | (2011.01) |
| *H01R 107/00* | (2006.01) |

(52) U.S. Cl.
CPC ............. *A61N 1/05* (2013.01); *A61N 1/3752* (2013.01); *H01R 13/621* (2013.01); *H01R 24/58* (2013.01); *H01R 2107/00* (2013.01); *H01R 2201/12* (2013.01)

(58) Field of Classification Search
CPC ...... A61N 1/05; A61N 1/3752; H01R 13/621; H01R 2107/00; H01R 2201/12; H01R 24/58
See application file for complete search history.

(56) References Cited

U.S. PATENT DOCUMENTS

| | | | |
|---|---|---|---|
| 3,222,471 | A | 12/1965 | Steinkamp |
| 3,601,747 | A | 8/1971 | Prall et al. |
| 3,718,142 | A | 2/1973 | Mulier |
| 3,757,789 | A | 9/1973 | Shanker |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — George Manuel
(74) *Attorney, Agent, or Firm* — Lowe Graham Jones PLLC; Bruce E. Black

(57) ABSTRACT

A connector to couple an electrical stimulation lead to a lead extension can include lead terminals and extension connector contacts that interlock with each other. Another connector can include lead terminals and extension connector contacts that form a hook and loop fastener. Yet another connector defines a lumen for receiving a proximal portion of an electrical stimulation lead and a side-loading slit extending along at least a portion of the longitudinal surface of the connector and extending inwardly to the lumen for side-loading the electrical stimulation lead into the lumen through the side-loading slit.

20 Claims, 9 Drawing Sheets

(56) References Cited

U.S. PATENT DOCUMENTS

| | | |
|---|---|---|
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |

(56) References Cited

U.S. PATENT DOCUMENTS

| | | |
|---|---|---|
| 6,671,553 B1 | 12/2003 | Helland et al. |
| 6,678,564 B2 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooj et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 * | 10/2007 | Cole ............... A61N 1/0553 607/116 |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,270,070 B2 | 2/2016 | Pianca |
| 9,289,596 B2 | 3/2016 | Leven |
| 9,352,147 B2 | 5/2016 | Nguyen-Stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,620 B2 | 11/2016 | Romero et al. |
| 9,504,839 B2 | 11/2016 | Leven |
| 9,656,093 B2 | 5/2017 | Villarta et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholt et al. |
| 2007/0042648 A1 | 2/2007 | Balsells |
| 2007/0142889 A1 | 6/2007 | Whitehurst et al. |
| 2007/0150036 A1 | 6/2007 | Anderson |

(56) References Cited

U.S. PATENT DOCUMENTS

| | | |
|---|---|---|
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0005829 A1* | 1/2011 | Pianca ............... A61N 1/05 174/74 R |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffitt et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0228692 A1 | 8/2016 | Steinke et al. |
| 2016/0296745 A1 | 10/2016 | Govea et al. |
| 2017/0072187 A1 | 3/2017 | Howard et al. |
| 2017/0143978 A1 | 5/2017 | Barker |
| 2017/0203104 A1 | 7/2017 | Nageri et al. |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

\* cited by examiner

CONNECTORS FOR ELECTRICAL STIMULATION SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/216,594, filed Sep. 10, 2015, which is incorporated herein by reference.

FIELD

The present invention is directed to the area of implantable electrical stimulation systems and methods of making and using the systems. The present invention is also directed to implantable electrical stimulation leads and connectors for connecting to a lead extension, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation system that includes an electrical stimulation lead and a lead extension. The electrical stimulation lead includes a lead body having a distal end portion, a proximal end, and a longitudinal length, electrodes disposed along the distal end portion of the lead body, a proximal connector body disposed at the proximal end of the lead body, terminals disposed along the proximal connector body, and conductors electrically coupling the terminals to the electrodes. The lead extension includes an extension body having a distal end, a proximal end portion, and a longitudinal length, terminal disposed along the proximal end portion of the extension body, a distal connector body disposed at the distal end of the extension body, conductive contacts disposed along the distal connector body, and conductors electrically coupling the terminals to the conductive contacts. The proximal connector body of the electrical stimulation lead and the distal connector body of the lead extension are configured and arranged to be joined together opposite each other to form a connector with the terminals of the electrical stimulation lead interlocking with, and electrically coupled to, the conductive contacts of the lead extension.

In at least some embodiments, either of the terminals or the conductive contacts each include a cut so that another of the terminals or the conductive contacts can slide into the cut for interlocking the terminals with the conductive contacts. In at least some embodiments, both the terminals and the conductive contacts each include a cut so that the terminals and the conductive contacts can slide into the cuts for interlocking the terminals with the conductive contacts.

In at least some embodiments, the electrical stimulation system further includes an outer sleeve configured and arranged to be disposed over the connector for maintenance of the joining of the proximal connector body of the electrical stimulation lead and the distal connector body of the lead extension. In at least some embodiments, each of the terminals and the conductive contacts includes an interlocking portion in a form of a portion of a ring. In at least some embodiments, each of the proximal connector body and the distal connector body have a form of a part of a cylinder and, when joined, the connector has a form of a cylinder.

Another embodiment is an electrical stimulation system that includes an electrical stimulation lead and a lead extension. The electrical stimulation lead includes a lead body having a distal end portion, a proximal end, and a longitudinal length, electrodes disposed along the distal end portion of the lead body, a proximal connector body disposed at the proximal end of the lead body, terminals disposed along the proximal connector body, and conductors electrically coupling the terminals to the electrodes. The lead extension includes an extension body having a distal end, a proximal end portion, and a longitudinal length, terminal disposed along the proximal end portion of the extension body, a distal connector body disposed at the distal end of the extension body, conductive contacts disposed along the distal connector body, and conductors electrically coupling the terminals to the conductive contacts. The proximal connector body of the electrical stimulation lead and the distal connector body of the lead extension are configured and arranged to be joined together opposite each other to form a connector with the terminals of the electrical stimulation lead and the conductive contacts of the lead extension jointly forming a conductive, hook and loop fastener to electrically and physically couple the terminals to the conductive contacts.

In at least some embodiments, the hook and loop fastener includes 1) one of a) the terminals of the electrical stimulation lead or b) the conductive contacts of the lead extension including a base and hooks extending from the base and 2) another of a) the terminals of the electrical stimulation lead or b) the conductive contacts of the lead extension including a base and loops extending from the base. In at least some embodiments, the conductive, hook and loop fastener includes a polymeric hook and loop fastener and a conductive coating disposed over the polymeric hook and loop fastener.

In at least some embodiments, the electrical stimulation system further includes an outer sleeve configured and arranged to be disposed over the connector for maintenance of the joining of the proximal connector body of the electrical stimulation lead and the distal connector body of the lead extension. In at least some embodiments, the electrical stimulation system further includes alignment features formed on both the proximal connector body and the distal connector body, wherein the alignment features jointly form a hook and loop fastener. In at least some embodiments, the alignment features are disposed around at least a portion of a perimeter of both the proximal connector body and the distal connector body.

A further embodiment is a lead extension for an electrical stimulation system that includes an extension body having a distal end, a proximal end portion, and a longitudinal length; terminals disposed along the proximal end portion of the extension body; and a distal connector disposed at the distal end of the extension body. The distal connector includes a proximal end, a distal end, and a longitudinal surface extending from the proximal end to the distal end. The distal connector defining a lumen for receiving a proximal portion of an electrical stimulation lead, an end aperture at the distal end of the distal connector from which a lead body of the electrical stimulation lead can extend, and a side-loading slit extending along at least a portion of the longitudinal surface and extending inwardly to the lumen and configured and arranged for side-loading the electrical stimulation lead into the lumen through the side-loading slit. The lead extension also includes conductive contacts disposed along the lumen of the distal connector, each of the conductive contacts having an opening aligned with the side-loading slit; and conductors electrically coupling the terminals to the conductive contacts.

In at least some embodiments, the lead extension further includes an outer sleeve configured and arranged to be disposed over the distal connector to cover the distal connector and a proximal portion of a stimulation lead, if any, disposed in the distal connector. In at least some embodiments, the outer sleeve includes a transverse lumen intersecting the lumen of the distal connector and configured and arranged to receive a fastener for securement of an electrical stimulation lead within the lumen of the distal connector.

In at least some embodiments, the distal connector includes a transverse lumen intersecting the lumen of the distal connector and configured and arranged to receive a fastener for securement of an electrical stimulation lead within the lumen of the distal connector. In at least some embodiments, the distal connector further includes a flap configured and arranged to fold over and cover the side-loading slot. In at least some embodiments, the flap includes a lip to at least partially fill the side-loading slot when the flap is folded over and covering the side-loading slot. In at least some embodiments, each of the conductor contacts is ring-shaped except for the opening.

Yet another embodiment is an electrical stimulation system that includes the lead extension described above and an electrical stimulation lead. The electrical stimulation lead includes a lead body having a distal end portion, a proximal end portion, and a longitudinal length, electrodes disposed along the distal end portion of the lead body, terminals disposed along the proximal end portion of the lead body, conductors electrically coupling the terminals to the electrodes; where the lumen of the lead extension is configured and arranged to receive the proximal end portion of the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads and connectors for connecting to a lead extension, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
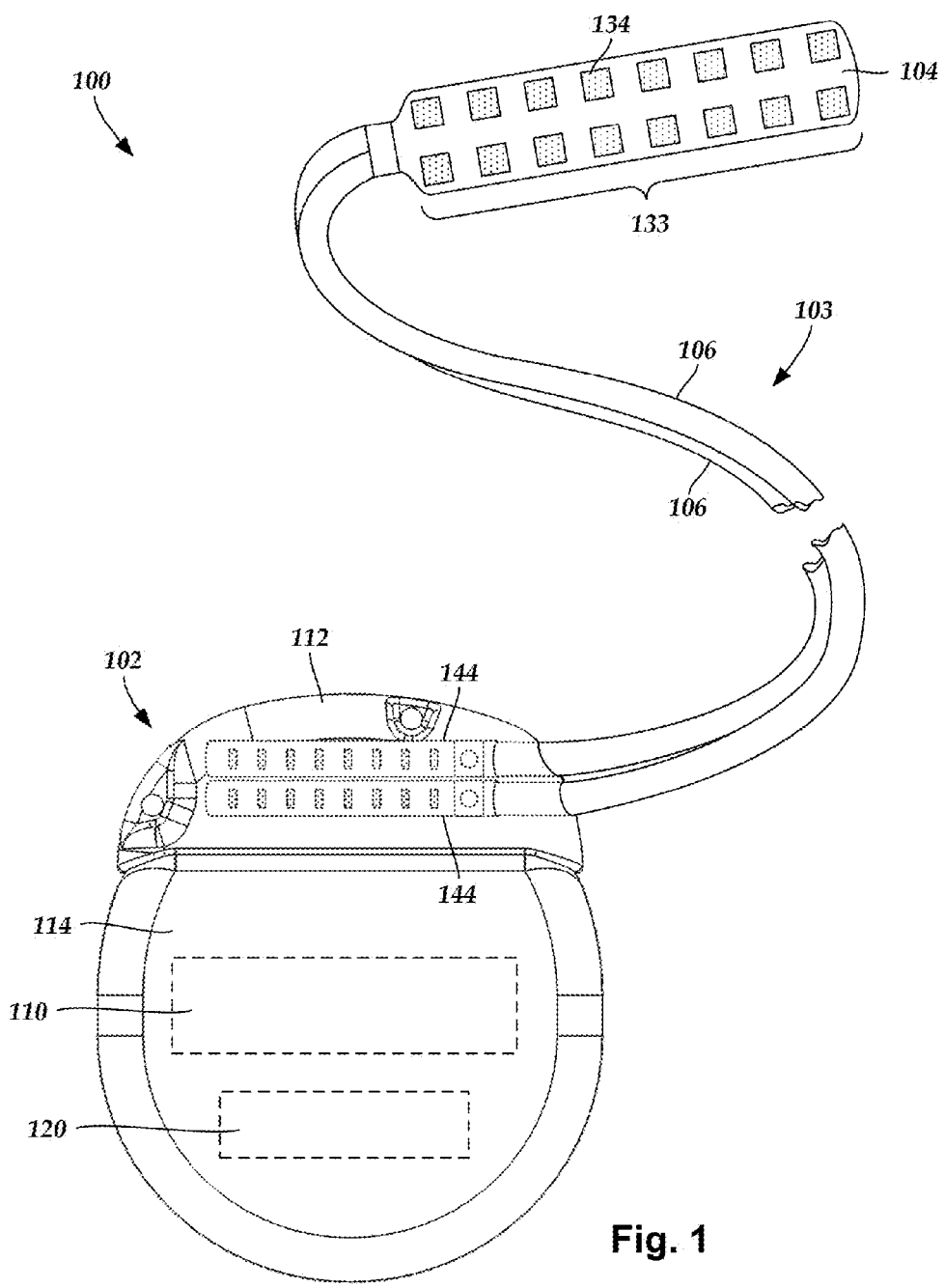
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
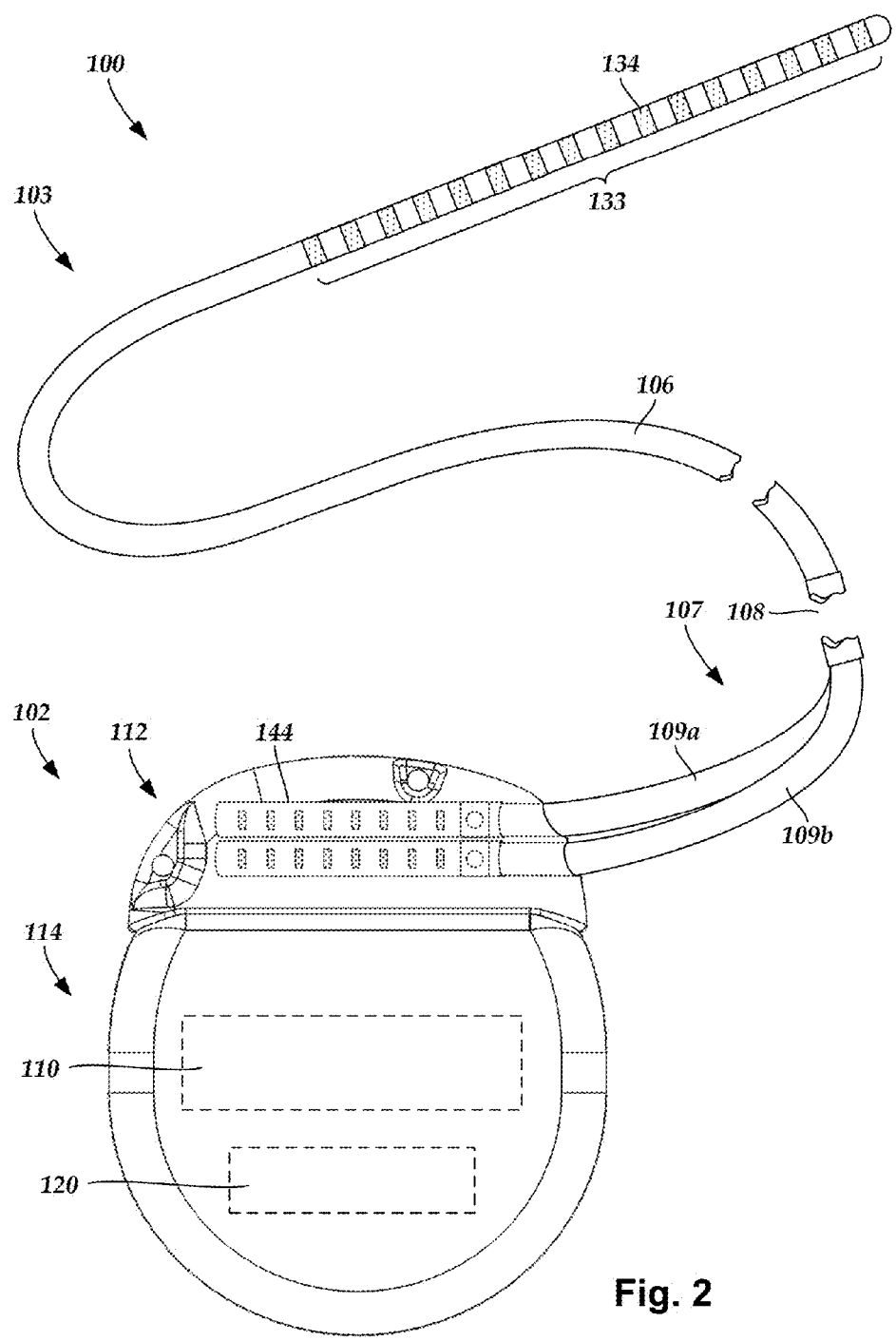
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, nickel titanium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
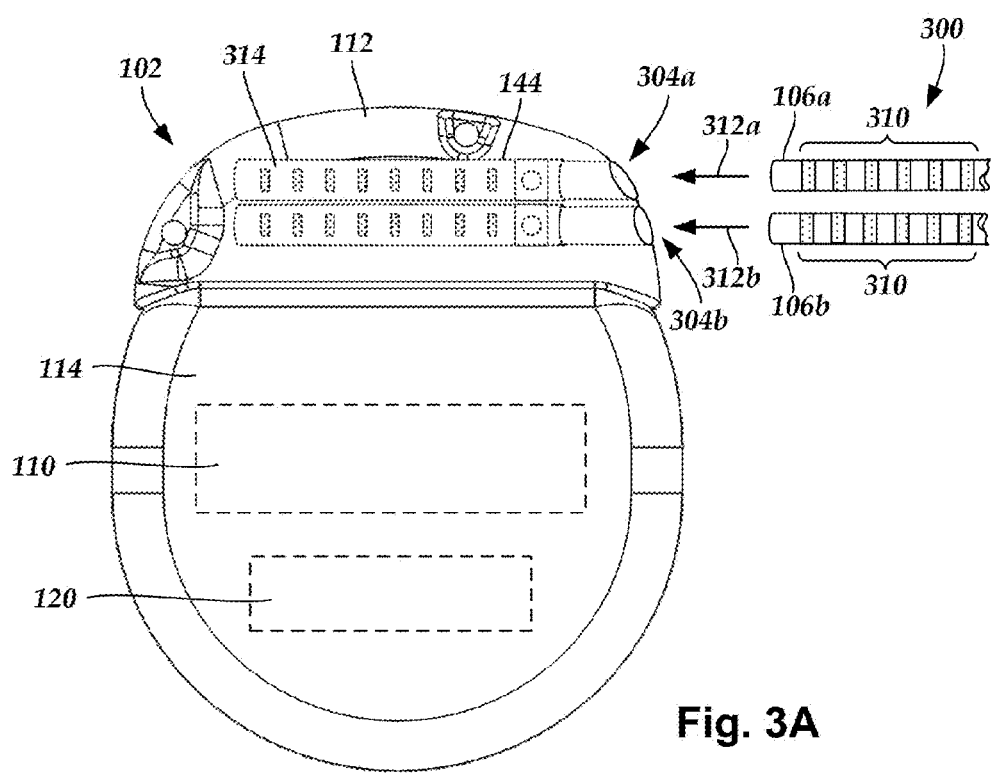
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
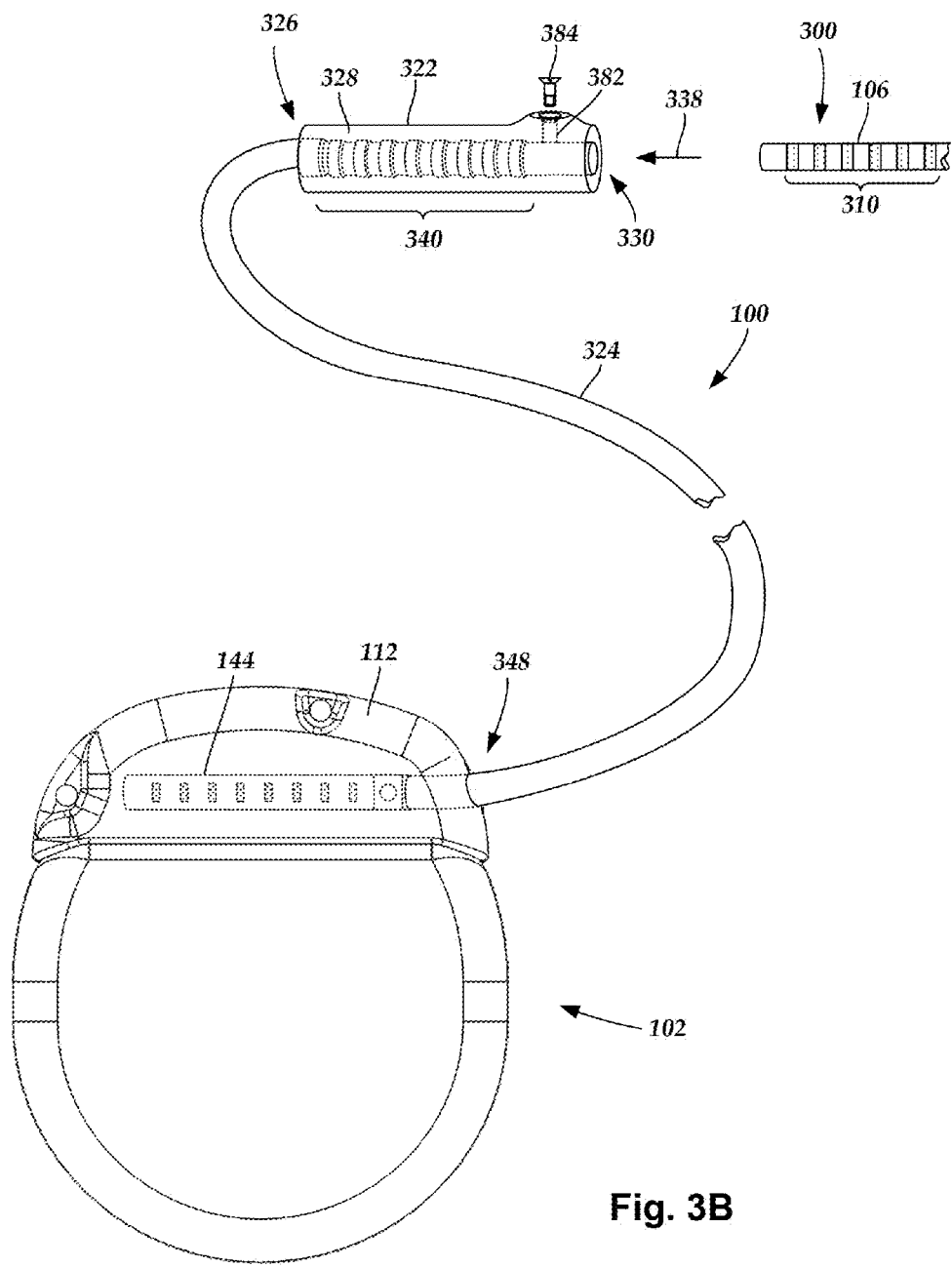
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2). In some embodiments, the lead extension connector 322 includes a transverse lumen 382 that allows a set crew 384 to be inserted and tightened against the lead 300 (or a retention sleeve on the lead) for securing the lead within the lead extension connector.

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Conventional lead extensions, and in particular, the connectors of the lead extension, may be large and bulky. In addition, there is a desire to increase conductor count so that the leads can have more electrodes which, at least in some instances, will require more contacts in a connector. In at least some embodiments, the connectors described below can fit more contacts into a patient friendly and physician friendly form factor. In at least some embodiments, the lead extensions and connector described below can provide a lower profile than conventional connectors even with increased conductor counts.

In at least some embodiments, the lead and lead extension can have interlocking contacts that couple together to form a connector and facilitate and maintain the coupling of the lead to the lead extension. Although the examples below are directed to the coupling of a lead to a lead extension, it will be recognized that these arrangements can be used to couple one lead extension to another lead extension (where, for example, the terminals and lead body of the lead, described below, are replaced by conductive contacts and a lead extension body of the lead extension). In other examples, the arrangements described below can be used to couple an operating room cable to a lead or lead extension or to couple an implantable pulse generator to a lead or lead extension.

Figure 4A:
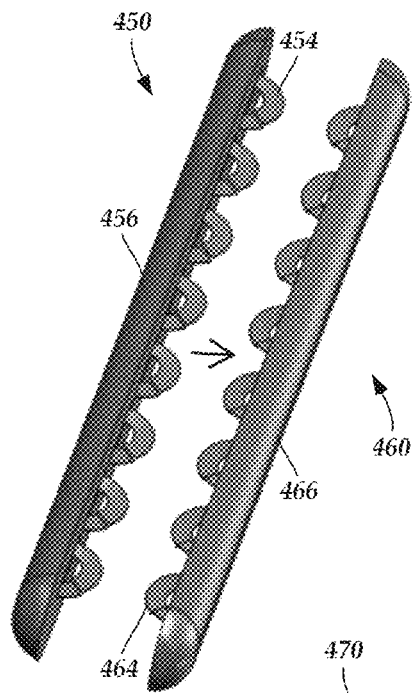
FIG. 4A is a schematic perspective view of one embodiment of a proximal connector of a lead and a distal connector of a lead extension, according to the invention.
Figure 4B:
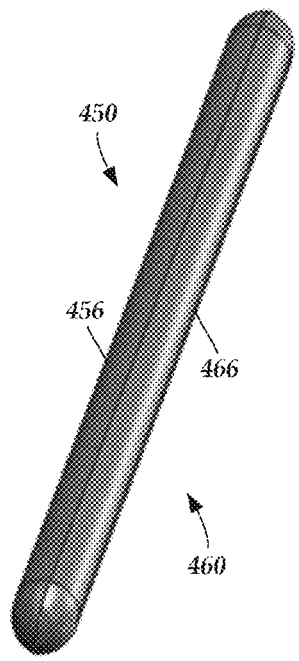
FIG. 4B is a schematic perspective view of the proximal connector and the distal connector of FIG. 4A coupled together, according to the invention.
Figure 4C:
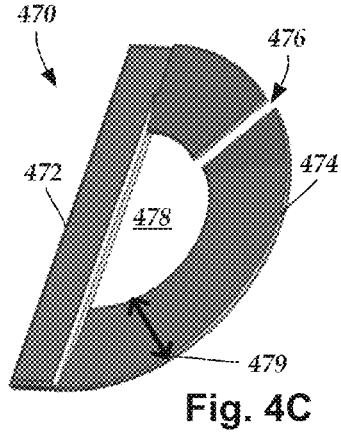
FIG. 4C is a schematic perspective view of one embodiment of a contact for use with the proximal connector or distal connector of FIG. 4A, according to the invention.
Figure 4D:
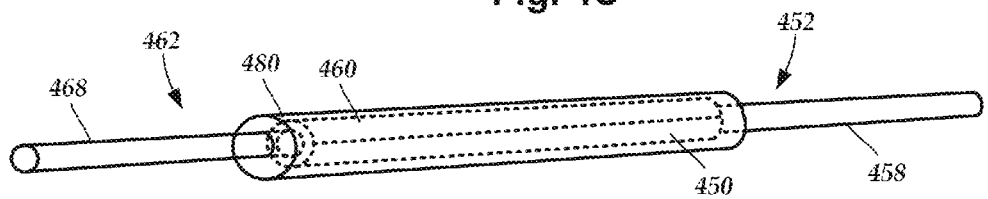
FIG. 4D is a schematic perspective view of the proximal connector and the distal connector of FIG. 4A coupled together with an outer sleeve, according to the invention.

FIGS. 4A-4D illustrate one embodiment of a proximal connector 450 of the proximal portion 452 (FIG. 4D) of a lead and a distal connector 460 of the distal portion 462 (FIG. 4D) of a lead extension. The proximal connector 450 of the lead includes terminals 454 coupled to a lead connector body 456 and the distal connector 460 of the lead extension includes conductive contacts 464 coupled to an extension connector body 466. A lead body 458 (a portion of which is illustrated in FIG. 4D) extends from the proximal connector 450 of the lead and an extension body 468 (a portion of which is illustrated in FIG. 4D) extends from the distal connector 460 of the lead extension. FIG. 4B illustrates the proximal connector 450 of the lead coupled to the distal connector 460 of the lead extension. In some embodiments, each of the proximal connector 450 and the distal connector 460 a The lead connector body 456 and extension connector body 466 can be made of any suitable biocompatible, non-conductive material including any of the materials described above for the lead body, such as, for example, silicone, polyurethane, polyetheretherketone ("PEEK"), epoxy, or the like or combinations thereof. In some embodiments, the lead connector body 456 and the lead body 458 are formed of the same material. In some embodiments, the extension connector body 466 and the extension body 468 are formed of the same material. In some embodiments, each of the proximal connector body 456 and the distal connector body 466 are in the form of a part of a cylinder and, when joined together (as illustrated in FIG. 4B), form a full cylinder. For example, each of the proximal connector body 456 and the distal connector body 466 are in the form of a half of a cylinder.

The terminals 454 of the lead and the conductive contacts 464 of the lead extension can be made so that they interlock with each other when the proximal connector 450 of the lead is coupled to the distal connector 460 of the lead extension. FIG. 4C illustrates one embodiment of contact 470 that can be used for both the terminals 454 of the lead and the conductive contacts 464 of the lead extension (as illustrated in FIG. 4A). The contact 470 is typically made of any conductive, biocompatible material. Examples of suitable materials include metals, alloys, conductive polymers, conductive carbon, and the like, as well as combinations thereof. In at least some embodiments, one or more of the contacts 470 are formed from one or more of: platinum, platinum iridium, palladium, palladium rhodium, nickel titanium, or titanium.

The contact 470 includes a connection portion 472, an interlocking portion 474, a cut 476 through the interlocking portion, and an optional aperture 478. The connector portion 472 is disposed at least partially within the lead connector body 456 or extension connector body 466 to hold the contact 470 in place within the respective connector body. In addition, one of the conductors, described above, is electrically coupled to the connector portion 472 to provide electrical connection between the contact 470 and an electrode, if the contact is part of a lead, or a terminal, if the contact is part of a lead extension. The coupling of the conductor to the connector portion 472 can be made by welding, soldering, or any other suitable coupling mechanism.

The interlocking portion 474 of contact 470 is designed to electrically couple with a corresponding interlocking portion of another contact in an opposing connector (e.g., proximal connector 450 or distal connector 460). In at least some embodiments, the interlocking portion 474 is in the form a portion of a ring (for example, half of a ring), as illustrated in FIG. 4C. The cut 476 extends into the interlocking portion 474 (and, at least in some embodiments, through the entire width, indicated by double-sided arrow 479, of the interlocking portion as illustrated in FIG. 4C) so that the interlocking portion of another contact can be inserted into the cut 476 and interlock the two contacts. In at least some embodiments, the contacts 454, 464 of both the proximal connector 450 and distal connector 460 have a cut into (or through the width of) the interlocking portions of those contacts. In other embodiments, the contacts 454, 464 of only one of the proximal connector 450 or the distal connector 460 have a cut into (or through the width of) the interlocking portions of those contacts and the contacts of the other one of the proximal connector or the distal connector do not have a cut.

Optionally, an outer sleeve 480 can be disposed (for example, slid) over the two connectors 450, 460, as illustrated in FIG. 4D. The outer sleeve 480 is formed of a biocompatible, non-conductive material such as, for example, silicone, polyurethane, or the like or combinations thereof. The outer sleeve 480 may facilitate sealing the connectors 450, 460 and may also provide electrical isolation for the terminals 454 and connector contacts 464. In at least some embodiments, when the connectors 450, 460 are implanted, one or more sutures may be wrapped around the connectors 450, 460 or the outer sleeve 480 for coupling to tissue or to maintain coupling of the connectors 450, 460.

Figure 5A:
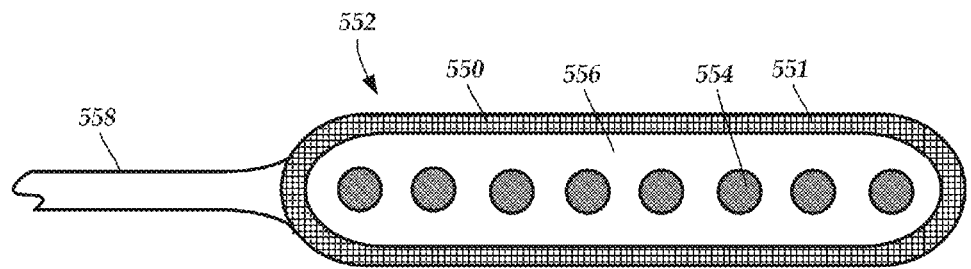
FIG. 5A is a schematic perspective view of one embodiment of a proximal connector of a lead, according to the invention.
Figure 5B:
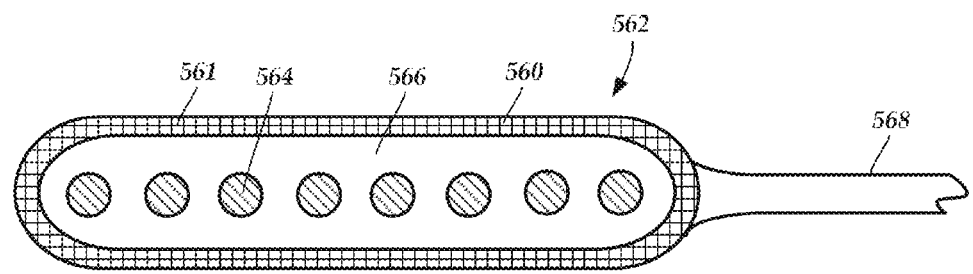
FIG. 5B is a schematic perspective view of one embodiment of a distal connector of a lead extension, according to the invention.
Figure 5C:
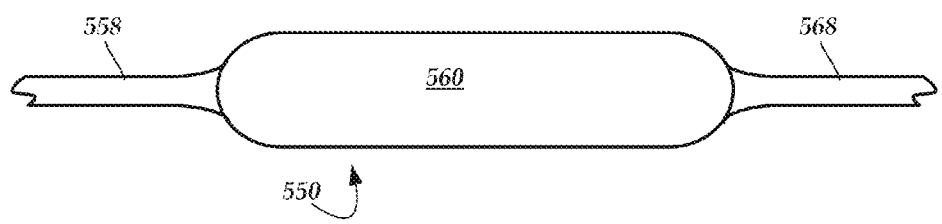
FIG. 5C is a schematic perspective view of the proximal connector of FIG. 5A and the distal connector of FIG. 5B coupled together, according to the invention.

FIGS. 5A-5C illustrate another embodiment with interlocking contacts. FIG. 5A illustrates a proximal portion 552 of a lead that includes a proximal connector 550, terminals 554 coupled to a lead connector body 556, and a portion of a lead body 558. FIG. 5B illustrates a distal portion 562 of a lead extension that includes a distal connector 560, conductive contacts 564 coupled to an extension connector body 566, and an extension body 568. FIG. 5C illustrates the proximal connector 550 of the lead coupled to the distal connector 560 of the lead extension.

The lead connector body 556 and extension connector body 566 can be made of any suitable biocompatible, non-conductive material including any of the materials described above for the lead body, such as, for example, silicone, polyurethane, polyetheretherketone ("PEEK"), epoxy, or the like or combinations thereof. In some embodiments, the lead connector body 556 and the lead body 558 are formed of the same material. In some embodiments, the extension connector body 566 and the extension body 568 are formed of the same material.

The terminals 554 and conductive contacts 564 together form a conductive, hook and loop fastener, similar to the hook and loop fasteners often referred to as Velcro™. Hook and loop fasteners are commonly made of polymeric materials which can be coated with metals, such as silver, platinum, platinum iridium, palladium, palladium rhodium, nickel titanium, titanium, graphene, or the like to make the fastener conductive. Alternatively or additionally, the conductive, hook and loop fastener can be formed using a conductive polymer. Either the terminals 554 or the conductive contacts 564 have conductive hooks extending from a conductive base and the other of the terminals 554 or the conductive contacts 564 have conductive loops extending from a conductive base. Alternatively, instead of a hook and loop fastener, the terminals 554 and conductive contacts 564 can include indentations and protrusions that interlock with each other.

Conductors, described above, extend from the lead body 558 and extension body 568 into the lead connector body 556 or extension connector body 566, respectively. The conductors are individually, electrically coupled to the conductive bases of the terminals 554 and conductive contact 564 to provide electrical connection with the electrode (in the case of a lead) or the terminal (in the case of a lead extension). The coupling of the conductors to the bases of the terminals 554 or conductive contacts 564 can be made by welding, soldering, or any other suitable coupling mechanism.

Optionally, the proximal connector 550 and the distal connector 560 can have alignment features 551, 561, respectively, that also form a hook and loop fastener that may or may not be conductive. Either the alignment feature 551 or the alignment feature 561 has hooks extending from a base and the other one of the alignment feature 551 or the alignment feature 561 has loops extending from a base. In at least some embodiments, such as those illustrated in FIGS. 5A and 5B, the alignment features 551, 561 extend around a perimeter of the proximal and distal connectors 550, 560, respectively. In other embodiments, the alignment features 551, 561 may only extend around a portion of the perimeter of the proximal and distal connectors 550, 560, respectively, or each of the alignment features 551, 561 may be formed in two or more separated segments spaced apart from each other around the perimeter of the proximal and distal connectors 550, 560, respectively, or in any other suitable arrangement on the proximal and distal connectors 550, 560.

Optionally, after the proximal and distal connectors 550, 560 are pressed together, an outer sleeve (similar to the outer sleeve 480 describe above) can then be disposed (for example, slid) over the proximal and distal connectors 550, 560. The outer sleeve is formed of a biocompatible, non-conductive material such as, for example, silicone, polyurethane, or the like or combinations thereof. The outer sleeve may facilitate sealing the connectors 550, 560 and may also provide electrical isolation for the terminals 554 and connector contacts 564. In at least some embodiments, when the connectors 550, 560 are implanted, one or more sutures may be wrapped around the connectors 550, 560 or the outer sleeve for coupling to tissue or to maintain coupling of the connectors 550, 560.

Figure 6A:
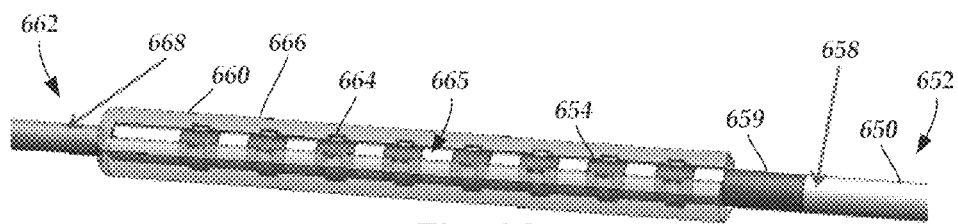
FIG. 6A is a schematic perspective view of one embodiment of a distal connector of a lead extension receiving a portion of lead, according to the invention.
Figure 6B:
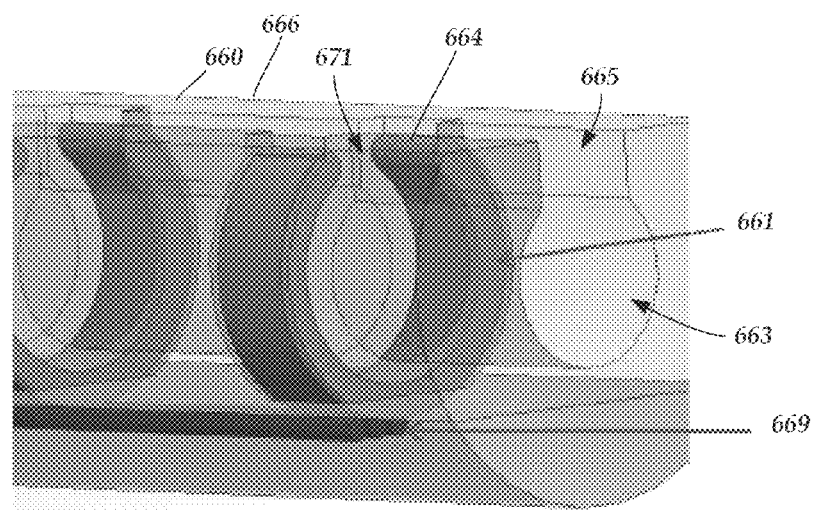
FIG. 6B is a schematic close-up view of a portion of the distal connector of FIG. 6A, according to the invention.

In another embodiment, a connector allows for side-loading of the proximal end of the lead into the connector instead of end-loading as illustrated in FIG. 3B. FIGS. 6A and 6B illustrate one embodiment of distal portion 662 of a lead extension with an extension body 668 and a connector 660 that includes an extension connector body 666 and conductive contacts 664 disposed in the extension connector body. FIG. 6B is a close-up view of a portion of the connector 660 and one of the conductive contacts 664. In FIG. 6A, a proximal portion 652 of a lead 650 is inserted into the connector 660. The lead includes a lead body 658, terminals 654, and an optional retention sleeve 659.

The extension connector body 666 of the connector 660 defines a lumen 661 to receive the lead 650 and an end aperture 663 from which the lead body 658 can extend, as illustrated in FIG. 6B. In addition, the extension connector body 666 includes a side-loading slit 665 extending from a longitudinal surface 667 of the connector 660 into the lumen 661 and extending along most (e.g., at least 50, 60, 70, 80, 90, 95% or more), or all, of the longitudinal length of the connector 660 so that the lead can be side-loaded into the lumen 661. In at least some embodiments, the side-loading slit 665 does not extend fully to the proximal end of the connector 660, as illustrated in FIG. 6A, but in other embodiments, the slit 665 can extend along the entire longitudinal length of the connector. The extension connector body 666 can be made of any suitable biocompatible, non-conductive material including any of the materials described above for the lead body, such as, for example, silicone, polyurethane, polyetheretherketone ("PEEK"), epoxy, or the like or combinations thereof. In some embodiments, the extension connector body 666 and the extension body 668 are formed of the same material.

The conductive contacts 664 are typically made of any conductive, biocompatible material. Examples of suitable materials include metals, alloys, conductive polymers, conductive carbon, and the like, as well as combinations thereof. In at least some embodiments, one or more of the conductive contacts 664 are formed from one or more of: platinum, platinum iridium, palladium, palladium rhodium, nickel titanium, or titanium. Each of the conductive contacts 664 is coupled to a conductor 669 to provide electrical connection between the conductive contact 664 and a terminal on the proximal end of the lead extension. The coupling of the conductor 669 to the conductive contact 664 can be made by welding, soldering, or any other suitable coupling mechanism.

The conductive contacts 664 are disposed along the lumen 661 of the connector and is formed with an opening 671 (FIG. 6B) that is aligned with the side-loading slit 665 so that the lead 650 can be inserted into the lumen through the openings in the conductive contact 664 with the terminals 654 making electrical contact with the conductive contacts 664. For example, the conductive contacts 664 can be horseshoe-shaped, U-shaped, partially ring-shaped with an opening in one part of the ring, or the like. In at last some embodiments, the conductive contacts 664 are clips that can clip around the lead 650 when the lead is inserted into the connector 660. In at least some embodiments, when pressing the lead 650 into the lumen 661 of the connector 660, the portion of the conductive contacts 664 near the opening 671 will expand temporarily to permit passage of the lead. In at least some embodiments, the inner diameter of the conductive contacts 664 can be undersized compared to diameter of the lead 650 or terminals 654 so that intimate electrical contact can be achieved between the conductive contacts 664 and lead terminals 654.

Figure 6C:
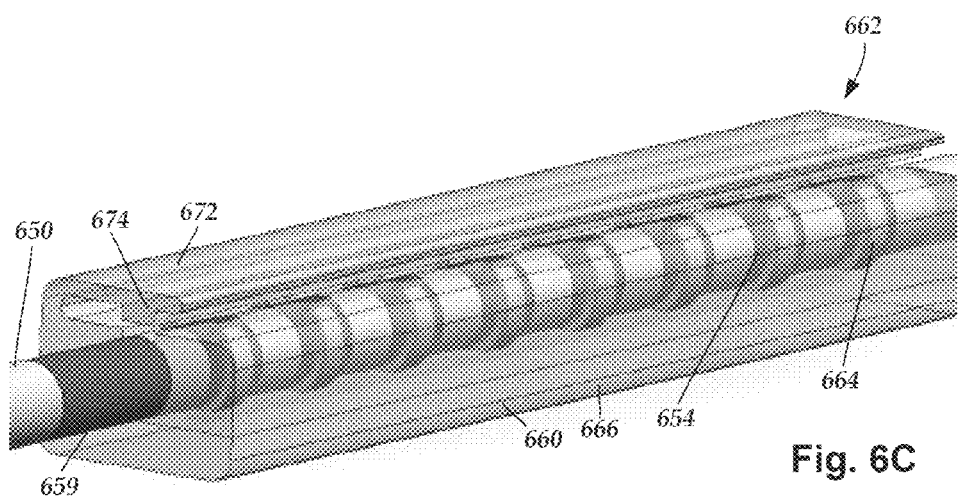
FIG. 6C is a schematic perspective view of another embodiment of a distal connector of a lead extension receiving a portion of lead, according to the invention.

In some embodiments, the connector 660 includes a flap 672 that can be folded over to cover the side-loading slit 665, as illustrated in FIG. 6C. The flap 672 optionally includes a lip 674 that can at least partially fill the side-loading slit 665. The flap 672 can be self-securing (for example, with the lip 674 frictionally or compressively held within the side-loading slit 665) or can be secured using sutures or the like or can be covered with an outer sleeve, as described below.

Figure 6D:
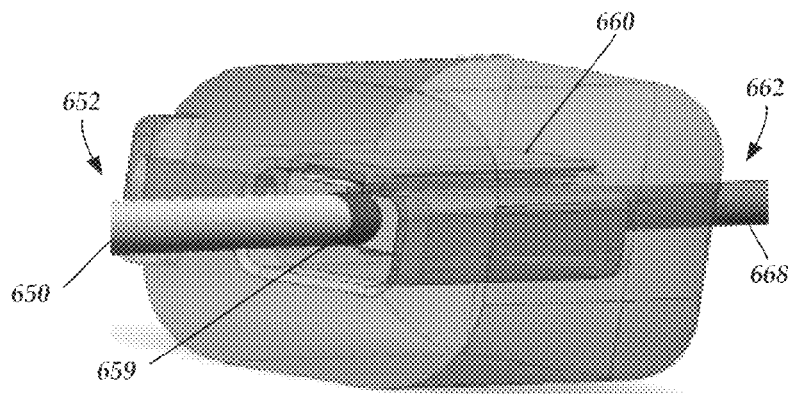
FIG. 6D is a schematic perspective view of the distal connector of FIG. 6C receiving a portion of lead and disposed in an outer sleeve, according to the invention.
Figure 6E:
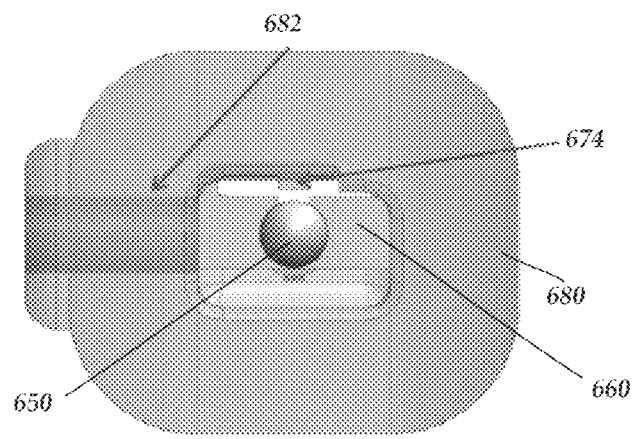
FIG. 6E is an end view of the arrangement of FIG. 6D, according to the invention.
Figure 6F:
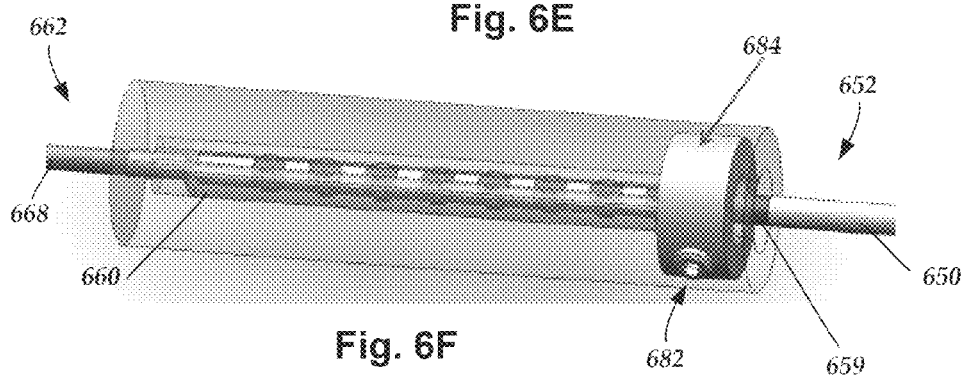
FIG. 6F is a schematic perspective view of the distal connector of FIGS. 6A and 6B receiving a portion of lead and disposed in an outer sleeve, according to the invention.

An outer sleeve 680 or cover can be slide over the connector 660, as illustrated in FIGS. 6D to 6F. FIGS. 6D and 6E illustrate one embodiment of an outer sleeve 680 for use with the connector 600 illustrated in FIG. 6C and FIG. 6F illustrates another embodiment of an outer sleeve 680 for use with the connector 600 illustrated in FIGS. 6A and 6B. The outer sleeve 680 is formed of a biocompatible, non-conductive material such as, for example, silicone, polyurethane, or the like or combinations thereof. The outer sleeve 680 may facilitate sealing the connector 660. In at least some embodiments, when the connector 660 is implanted, one or more sutures may be wrapped around the outer sleeve 680 for coupling to tissue or to maintain coupling of the connectors 660 to the lead 650. Optionally, the outer sleeve 680 can include a lip (similar to the lip 674 or flap 672) that can at least partially fill the side-loading slit 665.

The outer sleeve 680 can optionally include a transverse lumen 682 for receiving a set screw or other fastener (for example, set screw 384 in FIG. 3B) that can be engage the lead 650 (or, preferably, the retention sleeve 659 (FIG. 6A) of the lead) to secure the lead in the connector 660. In other embodiments, the traverse lumen can be provided in the connector 660 and a set screw or fastener can be inserted into the connector for lead securement. In some embodiments, the outer sleeve 680 may include a block 684 in which the transverse lumen 682 is formed and the set screw or other fastener is received. The block 684 may be made of a less flexible material than the remainder of the outer sleeve 680.

Figure 7:
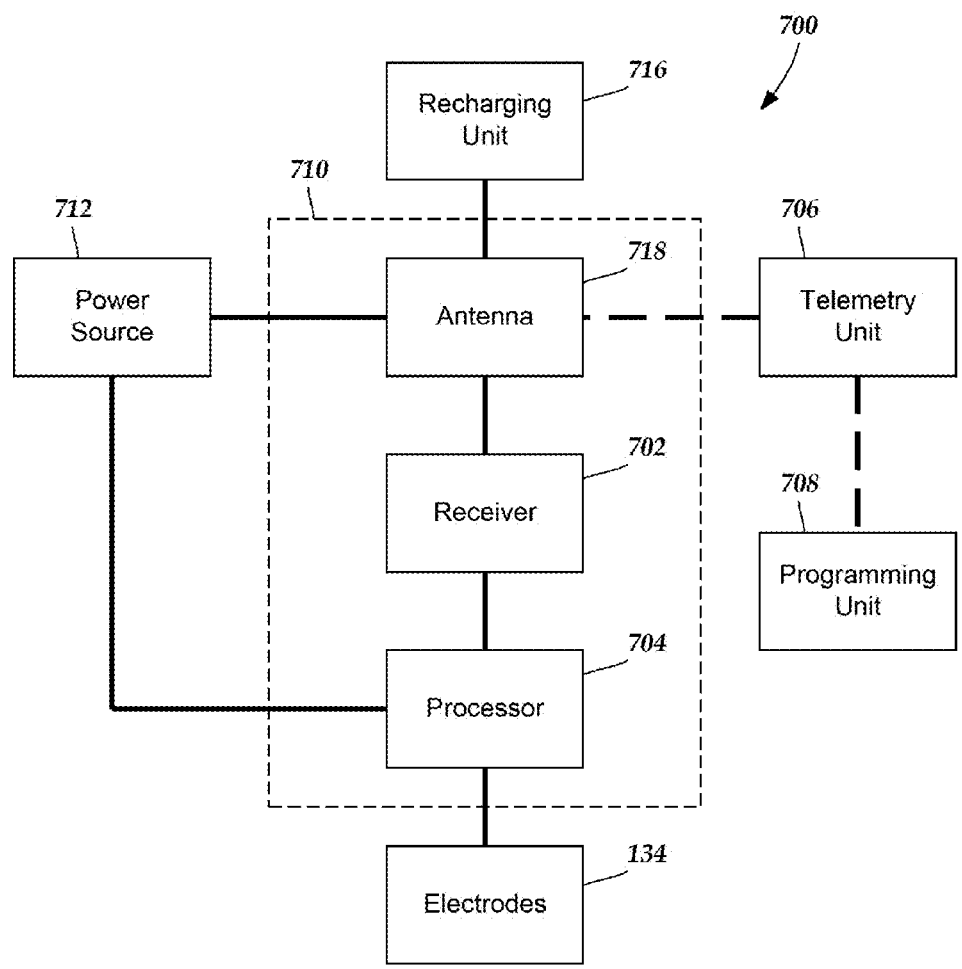
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
   an electrical stimulation lead, comprising
      a lead body having a distal end portion, a proximal end, and a longitudinal length,
      a plurality of electrodes disposed along the distal end portion of the lead body,
      a proximal connector body disposed at the proximal end of the lead body,
      a plurality of terminals disposed along the proximal connector body and extending laterally out of, and away from, the proximal connector body, and
      a plurality of conductors electrically coupling the plurality of terminals to the plurality of electrodes; and
   a lead extension, comprising an extension body having a distal end, a proximal end portion, and a longitudinal length,
a plurality of terminal disposed along the proximal end portion of the extension body,
a distal connector body disposed at the distal end of the extension body,
a plurality of conductive contacts disposed along the distal connector body and extending laterally out of, and away from, the distal connector body, and
a plurality of conductors electrically coupling the plurality of terminals to the plurality of conductive contacts;
wherein the proximal connector body of the electrical stimulation lead and the distal connector body of the lead extension are configured and arranged to be joined together opposite each other to form a connector with the terminals of the electrical stimulation lead interlocking with, and electrically coupled to, the conductive contacts of the lead extension.

2. The electrical stimulation system of claim 1, wherein either of the terminals or the conductive contacts each include a cut so that another of the terminals or the conductive contacts can slide into the cut for interlocking the terminals with the conductive contacts.

3. The electrical stimulation system of claim 1, wherein both the terminals and the conductive contacts each include a cut so that the terminals and the conductive contacts can slide into the cuts for interlocking the terminals with the conductive contacts.

4. The electrical stimulation system of claim 1, further comprising an outer sleeve configured and arranged to be disposed over the connector for maintenance of the joining of the proximal connector body of the electrical stimulation lead and the distal connector body of the lead extension.

5. The electrical stimulation system of claim 1, wherein each of the terminals and the conductive contacts comprises an interlocking portion in a form of a portion of a ring.

6. The electrical stimulation system of claim 1, wherein each of the proximal connector body and the distal connector body have a form of a half cylinder and, when joined, the connector has a form of a cylinder.

7. An electrical stimulation system, comprising:
an electrical stimulation lead, comprising
a lead body having a distal end portion, a proximal end, and a longitudinal length,
a plurality of electrodes disposed along the distal end portion of the lead body,
a proximal connector body disposed at the proximal end of the lead body,
a plurality of terminals disposed along the proximal connector body, and
a plurality of conductors electrically coupling the plurality of terminals to the plurality of electrodes; and
a lead extension, comprising
an extension body having a distal end, a proximal end portion, and a longitudinal length,
a plurality of terminals disposed along the proximal end portion of the extension body,
a distal connector body disposed at the distal end of the extension body,
a plurality of conductive contacts disposed along the distal connector body, and
a plurality of conductors electrically coupling the plurality of terminals to the plurality of conductive contacts;
wherein the proximal connector body of the electrical stimulation lead and the distal connector body of the lead extension are configured and arranged to be joined together opposite each other to form a connector with the terminals of the electrical stimulation lead and the conductive contacts of the lead extension jointly forming a conductive, hook and loop fastener to electrically and physically couple the terminals to the conductive contacts.

8. The electrical stimulation system of claim 7, wherein the hook and loop fastener comprises 1) one of a) the terminals of the electrical stimulation lead or b) the conductive contacts of the lead extension comprising a base and hooks extending from the base and 2) another of a) the terminals of the electrical stimulation lead or b) the conductive contacts of the lead extension comprising a base and loops extending from the base.

9. The electrical stimulation system of claim 7, wherein the conductive, hook and loop fastener comprises a polymeric hook and loop fastener and a conductive coating disposed over the polymeric hook and loop fastener.

10. The electrical stimulation system of claim 7, further comprising an outer sleeve configured and arranged to be disposed over the connector for maintenance of the joining of the proximal connector body of the electrical stimulation lead and the distal connector body of the lead extension.

11. The electrical stimulation system of claim 7, further comprising alignment features formed on both the proximal connector body and the distal connector body, wherein the alignment features jointly form a hook and loop fastener.

12. The electrical stimulation lead of claim 11, wherein the alignment features are disposed around at least a portion of a perimeter of both the proximal connector body and the distal connector body.

13. A lead extension for an electrical stimulation system, comprising:
an extension body having a distal end, a proximal end portion, and a longitudinal length;
a plurality of terminals disposed along the proximal end portion of the extension body;
a distal connector disposed at the distal end of the extension body, the distal connector comprising a proximal end, a distal end, and a longitudinal surface extending from the proximal end to the distal end of the distal connector, the distal connector defining a lumen for receiving a proximal portion of an electrical stimulation lead, an end aperture at the distal end of the distal connector from which a lead body of the electrical stimulation lead can extend, and a side-loading slit extending along at least a portion of the longitudinal surface and extending inwardly to the lumen and configured and arranged for side-loading the electrical stimulation lead into the lumen through the side-loading slit;
a plurality of conductive contacts disposed along the lumen of the distal connector, each of the conductive contacts having an opening aligned with the side-loading slit; and
a plurality of conductors electrically coupling the plurality of terminals to the plurality of conductive contacts.

14. The lead extension of claim 13, further comprising an outer sleeve configured and arranged to be disposed over the distal connector to cover the distal connector and a proximal portion of a stimulation lead, if any, disposed in the distal connector.

15. The lead extension of claim 14, wherein the outer sleeve comprises a transverse lumen intersecting the lumen of the distal connector and configured and arranged to receive a fastener for securement of an electrical stimulation lead within the lumen of the distal connector.

16. The lead extension of claim 13, wherein the distal connector comprises a transverse lumen intersecting the lumen of the distal connector and configured and arranged to receive a fastener for securement of an electrical stimulation lead within the lumen of the distal connector.

17. The lead extension of claim 13, wherein the distal connector further comprises a flap configured and arranged to fold over and cover the side-loading slit.

18. The lead extension of claim 17, wherein the flap comprises a lip to at least partially fill the side-loading slit when the flap is folded over and covering the side-loading slit.

19. The lead extension of claim 13, wherein each of the conductor contacts is ring-shaped except for the opening.

20. An electrical stimulation system, comprising:
the lead extension of claim 13; and
an electrical stimulation lead comprising
    a lead body having a distal end portion, a proximal end portion, and a longitudinal length,
    a plurality of electrodes disposed along the distal end portion of the lead body,
    a plurality of terminals disposed along the proximal end portion of the lead body,
    a plurality of conductors electrically coupling the plurality of terminals to the plurality of electrodes;
wherein the lumen of the lead extension is configured and arranged to receive the proximal end portion of the electrical stimulation lead.

\* \* \* \* \*